(12) United States Patent
Callne

(10) Patent No.: US 6,925,719 B2
(45) Date of Patent: Aug. 9, 2005

(54) POWERED COPING SAW

(76) Inventor: Lars Callne, 1744 Arbolita La., Fallbrook, CA (US) 92028

( * ) Notice: Subject to any disclaimer, the term of this patent is extended or adjusted under 35 U.S.C. 154(b) by 0 days.

(21) Appl. No.: 10/725,921

(22) Filed: Dec. 1, 2003

(65) Prior Publication Data

US 2005/0115085 A1     Jun. 2, 2005

(51) Int. Cl.⁷ ............................................. B23D 49/16
(52) U.S. Cl. ............................. 30/392; 30/509; 30/507
(58) Field of Search ....................... 30/338, 339, 380, 30/392, 507, 509, 394; 606/176, 177, 178

(56) References Cited

U.S. PATENT DOCUMENTS

| | | | |
|---|---|---|---|
| 1,324,032 A | | 12/1919 | Buell et al. |
| 1,661,217 A | | 3/1928 | Farrell |
| 1,775,692 A | * | 9/1930 | Plut ............................ 30/394 |
| 2,206,614 A | * | 7/1940 | O'Hern ....................... 30/392 |
| 2,330,618 A | * | 9/1943 | Plumb ......................... 30/371 |
| 2,457,829 A | | 1/1949 | Miller |
| 2,753,898 A | | 7/1956 | MacFarland |
| 4,949,464 A | | 8/1990 | Adomatis |
| 5,027,518 A | | 7/1991 | Adomatis |
| 5,044,254 A | * | 9/1991 | Miller et al. .................. 91/277 |
| 5,084,978 A | * | 2/1992 | McReynolds ................. 30/517 |
| 5,313,709 A | | 5/1994 | Pabon-Delgado |
| 5,369,887 A | | 12/1994 | Keevers |
| 5,529,532 A | * | 6/1996 | Desrosiers ................... 451/344 |
| 5,607,265 A | | 3/1997 | Lane |
| 5,870,829 A | * | 2/1999 | Gugel et al. ................... 30/392 |
| 5,924,209 A | | 7/1999 | Ward |
| 6,256,891 B1 | | 7/2001 | Van Camp et al. |
| 6,357,123 B1 | | 3/2002 | Manuel |

* cited by examiner

Primary Examiner—Hwei-Siu Payer
(74) Attorney, Agent, or Firm—Calif Tervo

(57) ABSTRACT

An elongate, cylindrical hand-held powered coping saw adapted for making thin cuts of short length, such as for cutting individual dies from a full arch dental model generally includes a blade assembly, a housing, a rotary motor having a drive shaft, a piston for driving the blade assembly, and a motion converter connecting the drive shaft to the piston for converting rotary motion of the drive shaft into reciprocating linear motion of the piston. Preferably, the blade stroke length is less than the distance between opposing U-sections of a full dental arch model along a cut line.

12 Claims, 1 Drawing Sheet

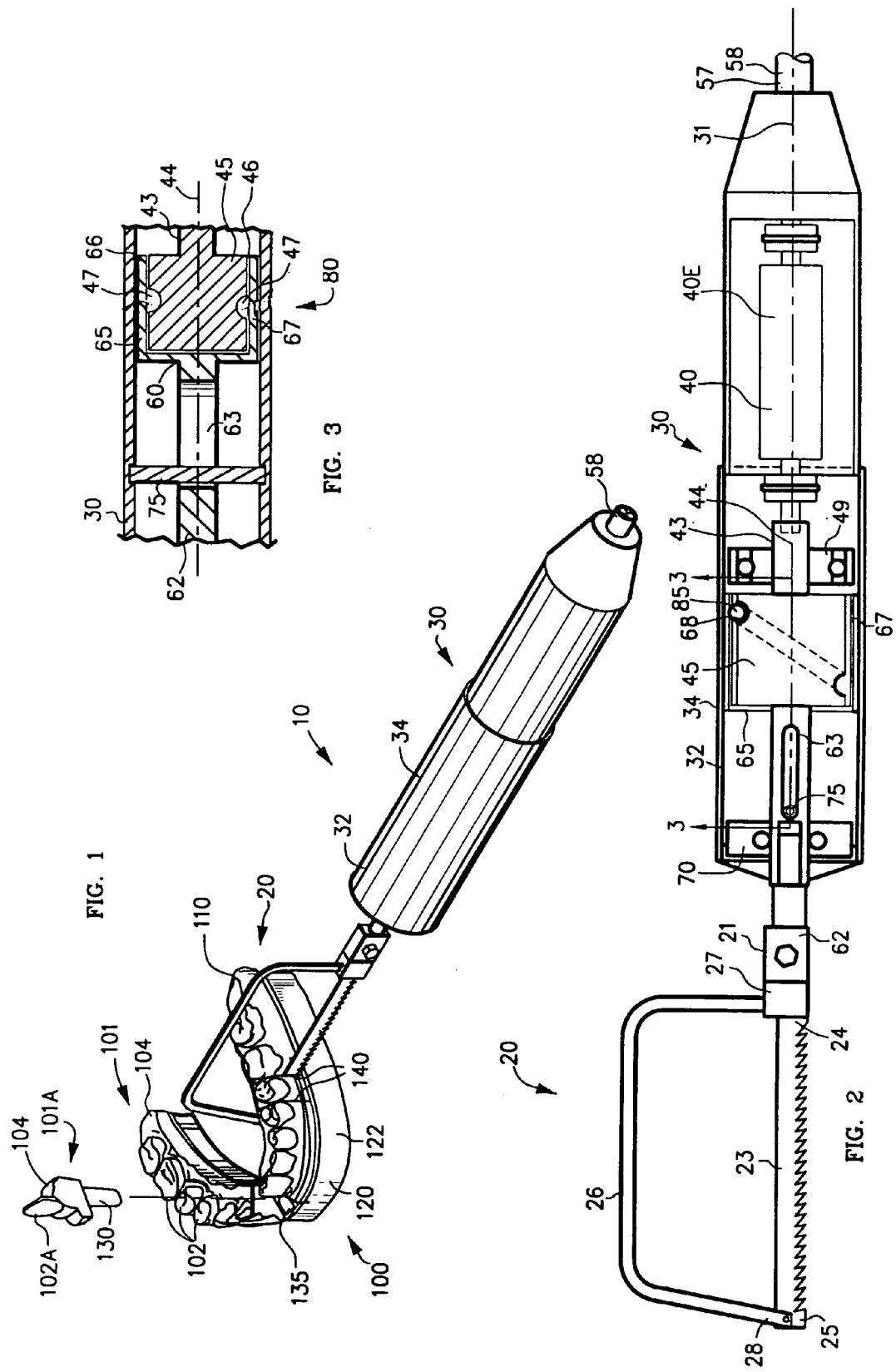

POWERED COPING SAW

FIELD OF THE INVENTION

This invention relates in general to a saw, and more specifically to a powered coping saw adapted for making thin cuts such as cutting individual dies from a dental model.

BACKGROUND OF THE INVENTION

To accurately form and position false teeth or caps, a dentist makes a negative impression of the patient's teeth. The impression is generally of a full arch or of a quadrant, that is of a half arch. This impression serves as a mold for making a dental model.

Dental models can be made from the negative mold in several manners. FIG. 1 is an exemplary dental model 100 generally representative of the methods. FIG. 1 is a top perspective view of a full arch dental model 100 including a positive die 101 of the teeth 102 and gums 104. An individual die 101A of an individual tooth 102A is shown cut out and removed.

To make the dental model 100 of FIG. 1, curable stone 110 is poured into the negative impression up to a point approximating the patient's gum line. An arch plate 120 includes an arch-shaped body 122 including a plurality of holes 135 distributed over the arch and removable protruding pins 130 in holes 135. Arch plate 120 is pressed into the wet stone in the negative impression such that pins 130 protrude into model gums 104. Arch plate 120 is typically made of strong plastic.

After curing, removal from the impression, and some trimming, dental model 100 results. Pins 130 protrude up into the stone gum 104 and body 122 underlies gum 104. Individual dies 101A of a tooth 102A are made by cutting on each side of tooth 102A down to body 122. Individual die 101A can be removed. Pins 130 provide for individual dies 101A to be reinserted in holes 135 of body 122 of arch plate 120 exactly the same place in dental model 100 for testing. Individual die 101A could include more that one tooth 102.

Conventionally, individual dies 101A are cut out with a manual coping saw. A coping saw is used because the saw blade must be very thin so as to destroy as little of the model as possible. The thinness of the blade necessitates that the blade is tensioned at both ends. The cutting out of individual dies 101A is very time consuming.

Therefore, there has been a need for an improved cutting device for more quickly cutting out individual dies 101A from a dental model.

BRIEF DESCRIPTION OF THE DRAWINGS

FIG. 1 is a perspective view of a preferred embodiment of the powered hand-held coping saw of the invention shown in use cutting a dental model. An individual die is shown in exploded view.

FIG. 2 is a side elevation view of the saw of FIG. 1 with the housing in cross-section.

FIG. 3 is a cross-sectional view on line 3—3 of FIG. 2 of the rotary motion to reciprocating motion converter.

DETAILED DESCRIPTION OF THE INVENTION

FIG. 1 is a perspective view of a preferred embodiment of the powered hand-held coping saw 10 of the invention shown in use cutting a full arch dental model 100. Dental model 100 includes a positive die 101 of a full dental arch including gums 104, a plurality of teeth 102 and an arch plate 120 connected to die 101. Arch plate 120 includes a body 122 defining holes 135 for containing removable pins 130. Full arch model 100 is roughly U-shaped in top view with opposing left and right sections. Shown in exploded view is an individual die 101A of an individual tooth 102A as it would be cut out and removed for working. Cut lines 140 are shown on either side of another individual die to be cut out. It can be seen that extensions of some cut lines 140 between teeth 102 would encounter the opposing arch section.

Looking also at FIGS. 2 and 3, FIG. 2 is a side elevation view of saw 10 of FIG. 1 with housing 30 in cross-section and FIG. 3 is a cross-sectional view on line 3—3 of FIG. 2 of rotary motion to reciprocating motion converter 80.

Coping saw 10 is designed for cutting individual dies 101A from dental model 100 along cut lines 140. Saw 10 generally includes a blade assembly 20, a housing 30, a rotary motor 40, a piston 60, and motion converter 80.

Blade assembly 20 has a proximal end 21 and includes a blade 23 and frame 26. Blade 23 is elongate and has a longitudinal axis. Blade 23 has a lower cutting edge and a thickness adapted for cutting individual dies 101A from model 100. This means that blade 23 is very thin so as to cut between individual teeth 102A and remove as little material as possible. Blade 23 has a proximal end 24 and a distal end 25. Frame 26 is rigid and includes a proximal end 27 connected to proximal end 24 of blade 23 and a distal end 28 connected to distal end 25 of blade 23 such that frame 26 supports blade 23 in tension. A conventional three-sided frame is shown.

Housing 30 is generally an elongate hollow cylinder with a longitudinal axis 31 and an outside surface 32 adapted as a handle 34 for holding saw 10 in a user's hand.

Rotary motor 40, such as an electric motor 40E, is mounted within housing 30. Power means 57, such as electrical cord 58, provides power for motor 40. Other power means 57 are contemplated including a battery, pneumatic line or hydraulic line. Electric motor 40E includes a drive shaft 43, rotating about a shaft axis 44, including a front end 45. Preferably, drive shaft axis 44 is parallel to housing axis 31 and, more preferably, is co-incident with it. Means, such as bearings 49, rotatably mount drive shaft 43 to housing 30.

Piston 60 includes a front end 62 connected to proximal end 21 of blade assembly 20 and rear end 65. Piston 60 is slideably and non-rotatably supported in housing 30. Means, such as bearing 70, connected to housing 30 slidingly mounts piston 60 to move in a direction parallel to housing axis 31. Means, such as pin 75 connected to housing 30 and disposed through elongate bore 63 in piston 60, prevents piston from rotation. Piston front end 62 moves blade assembly 20 along the longitudinal axis of blade 23 coincident with piston movement. Preferably, piston 60 moves parallel to housing axis 31.

Motion converter means 80 connects front end 45 of drive shaft 43 to rear end 65 of piston 60 for converting rotary motion of drive shaft 43 into reciprocating linear motion of piston 60. Motion converters of various configurations are well-known in the art. U.S. Pat. No. 5,607,265 shows several forms. A typical motion converter includes a rotary member having an elliptical or cam feature, and the saw includes a follower for following on the cam feature. In the exemplary embodiment, motion converter means 80 includes an exterior surface 46 on drive shaft front end 45 including a circumferential raceway 47 in a plane at an angle to the shaft axis 44 and a cap 66 on rear end 65 of piston 60 having an inside surface 67. Coupling means, such as hemispherical orifice 68 in interior surface 67 of cap 66 containing ball bearing 85, coupling raceway 47 and hemispherical orifice 68, couples drive shaft 43 with piston 60 to move piston 60. In this instance, raceway is semicircular in cross-section. The longitudinal distance between the forward extent of raceway 47 and rearward extent of raceway 47 determines the stroke length of blade 23. The stroke length of blade 23 is less than the distance between opposing U-sections along a cut line such that distal ends 25, 28 can reciprocate within the U-shaped arch model 100 so as to not strike the opposing arch section.

Having described the invention, it can be seen that it provides a very convenient tool for the more efficient cutting of thin cuts such as between teeth in a die.

Although a particular embodiment of the invention has been illustrated and described, various changes may be made in the form, composition, construction, and arrangement of the parts herein without sacrificing any of its advantages. Therefore, it is to be understood that all matter herein is to be interpreted as illustrative and not in any limiting sense, and it is intended to cover in the appended claims such modifications as come within the true spirit and scope of the invention.

I claim:

1. A saw including:
   a blade assembly having a proximal end; said blade assembly including:
      an elongate, thin blade having a longitudinal axis including:
         a proximal end; and
         a distal end; and
      a rigid frame including:
         a proximal end connected to said proximal end of said blade; and
         a distal end connected to said distal end of said blade; said frame for supporting said blade in tension;
   a housing including:
      handle means for holding said saw in a hand;
   a rotary motor mounted to said housing including:
      a drive shaft rotating about a shaft axis including:
         a front end;
   power means for powering said motor;
   a piston slideably and non-rotatably supported in said housing including:
      a front end connected to said proximal end of said blade assembly for moving said blade assembly along the longitudinal axis of said blade coincident with piston movement; and
      a rear end; and
   motion converter means for connecting said front end of said drive shaft to said rear end of said piston for converting rotary motion of said drive shaft into reciprocating linear motion of said piston; said motion converter means including:
      an exterior surface on said drive shaft front end including:
         a circumferential raceway in a plane at an angle to the shaft axis;
      a cap on said rear end of said piston having an inside surface; said cap fitting over said exterior surface of said front end of said drive shaft; and
      coupling means moving in said raceway for coupling with said cap to move said cap.

2. The saw of claim 1 wherein:
   said circumferential raceway is semicircular in cross-section; and
   said coupling means includes:
      a hemispherical orifice in said inside surface of said cap; and
      a ball bearing coupling said raceway and said hemispherical orifice.

3. A saw including:
   a blade assembly having a proximal end; said blade assembly including:
      an elongate, thin blade having a longitudinal axis including:
         a proximal end; and
         a distal end; and
      a rigid frame including:
         a proximal end connected to said proximal end of said blade; and
         a distal end connected to said distal end of said blade; said frame for supporting said blade in tension;
   a generally cylindrical, elongate housing having a longitudinal axis and an outside surface adapted for holding said saw in a hand;
   a rotary motor mounted within said housing including:
      a drive shaft rotating about a shaft axis; the shaft axis parallel to the housing axis; said drive shaft including:
         a front end;
   power means for powering said motor;
   a piston slideably and non-rotatably supported in said housing so as to be movable parallel to the housing axis; including:
      a front end connected to said proximal end of said blade assembly for moving said blade assembly along the longitudinal axis of said blade coincident with piston movement; and
      a rear end; and
   motion converter means for connecting said front end of said drive shaft to said rear end of said piston for converting rotary motion of said drive shaft into reciprocating linear motion of said piston; said motion converter means including:
      an exterior surface on said drive shaft front end including:
         a circumferential raceway in a plane at an angle to the shaft axis;
      a cap on said rear end of said piston having an inside surface; said cap fitting over said exterior surface of said front end of said drive shaft; and
      coupling means moving in said raceway for coupling with said cap to move said cap.

4. The saw of claim 3 wherein:
   said circumferential raceway is semicircular in cross-section; and
   said coupling means includes:
      a hemispherical orifice in said inside surface of said cap; and
      a ball bearing coupling said raceway and said hemispherical orifice.

5. The saw of claim 3 wherein:
   said motor is an electric motor.

6. The saw of claim 5 wherein:
   said power means is an electrical cord.

7. In combination:
a full dental arch model including:
   a positive die of a full dental arch including:
   gums; and
   a plurality of teeth; and
   an arch plate connected to said die; said full arch model being U-shaped in top view with opposing left and right sections;
a coping saw for cutting individual dies from said dental model including:
a blade assembly having a proximal end; said blade assembly including:
   an elongate, blade having a longitudinal axis and having a thickness adapted for cutting individual dies from said model including
      a proximal end; and
      a distal end; and
   a rigid frame including:
      a proximal end connected to said proximal end of said blade; and
      a distal end connected to said distal end of said blade; said frame for supporting said blade in tension;
a housing including:
   handle means for holding said saw in a hand,
a rotary motor mounted to said housing including:
   a drive shaft rotating about a shaft axis including:
      a front end;
power means for powering said motor;
a piston slideably and non-rotatably supported in said housing including:
   a front end connected to said blade assembly for moving said blade assembly along the longitudinal axis of said blade coincident with piston movement; and
   a rear end; and
motion converter means for connecting said front end of said drive shaft to said rear end of said piston for converting rotary motion of said drive shaft into reciprocating linear motion of said piston resulting in a stroke length of said blade assembly of less than the distance between opposing U-sections along a cut line;
said motion converter means including:
   an exterior surface on said drive shaft front end including:
      a circumferential raceway in a plane at an angle to the shaft axis;
   a cap on said rear end of said piston having an inside surface; said cap fitting over said exterior surface of said front end of said drive shaft; and
   coupling means moving in said raceway for coupling with said cap to move said cap.

8. The combination of claim 7 wherein:
said housing is generally cylindrical and elongate having a longitudinal axis and an outside surface adapted for holding said saw in a hand.

9. The combination of claim 8 wherein:
the shaft axis of said drive shaft is parallel to the housing axis; and
said piston moves parallel to the housing axis.

10. The combination of claim 7 wherein:
said circumferential raceway is semicircular in cross-section; and
said coupling means includes:
   a hemispherical orifice in said inside surface of said cap; and
   a ball bearing coupling said raceway and said hemispherical orifice.

11. The combination of claim 7 wherein:
said motor is an electric motor.

12. The combination of claim 11 wherein:
said power means is an electrical cord.

* * * * *